(12) United States Patent
Deng et al.

(10) Patent No.: US 9,615,725 B2
(45) Date of Patent: Apr. 11, 2017

(54) TAMPER-EVIDENT CAMERA ENCLOSURE

(71) Applicants: Wenjie Deng, San Jose, CA (US); William H. L. Chang, Milpitas, CA (US); Dai D. Tong, San Jose, CA (US)

(72) Inventors: Wenjie Deng, San Jose, CA (US); William H. L. Chang, Milpitas, CA (US); Dai D. Tong, San Jose, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 323 days.

(21) Appl. No.: 14/195,998

(22) Filed: Mar. 4, 2014

(65) Prior Publication Data

US 2014/0275781 A1    Sep. 18, 2014

Related U.S. Application Data

(60) Provisional application No. 61/782,099, filed on Mar. 14, 2013.

(51) Int. Cl.
*A61B 1/04*    (2006.01)
*B65D 43/00*    (2006.01)
(Continued)

(52) U.S. Cl.
CPC ........ *A61B 1/0011* (2013.01); *A61B 1/00066* (2013.01); *A61B 1/00142* (2013.01); *A61B 1/042* (2013.01); *G02B 23/2484* (2013.01); *B65D 43/0235* (2013.01); *Y10T 29/49826* (2015.01)

(58) Field of Classification Search
CPC .............. A61B 1/0011; A61B 1/00121; A61B 1/00128; A61B 1/00066; A61B 1/042; G02B 23/2484; B65D 43/0235; B65D 43/0229; Y10T 29/49863; Y10T 29/49876; Y10T 29/49913
USPC .... 220/259.3, 294, 298, 300, 308, 305, 788, 220/789, 621, 345.3
See application file for complete search history.

(56) References Cited

U.S. PATENT DOCUMENTS 4,310,213 A * 1/1982 Fetterolf, Sr. ........ H01R 13/516
439/320
4,590,923 A * 5/1986 Watanabe .......... A61B 1/00048
348/65
(Continued)

FOREIGN PATENT DOCUMENTS

CA    2 605 485 A1    10/2006
ES    2 013 370 A6    5/1990
(Continued)

OTHER PUBLICATIONS

Stryker 1288 HD camera enclosure redacted engineering drawings (3 pages).
(Continued)

*Primary Examiner* — John P Leubecker
(74) *Attorney, Agent, or Firm* — Flynn, Thiel, Boutell & Tanis, P.C.

(57) ABSTRACT

A housing for an instrument such as an endoscopic camera head is provided. The housing includes at least two parts which are attachable to each other by using tabs and grooves, creating a sealed and tamper-evident housing without the use of externally exposed fasteners. A tool for attaching the two parts and a method of its use are also provided.

11 Claims, 12 Drawing Sheets

(51) Int. Cl.
*A61B 1/00* (2006.01)
*G02B 23/24* (2006.01)
*B65D 43/02* (2006.01)

(56) References Cited

U.S. PATENT DOCUMENTS

| | | | |
|---|---|---|---|
| 4,600,940 A * | 7/1986 | Sluyter | A61B 1/042 348/73 |
| 4,756,304 A * | 7/1988 | Watanabe | A61B 1/00142 600/112 |
| 4,877,930 A | 10/1989 | Fukuma | |
| 4,930,656 A * | 6/1990 | Blanchette | B65D 43/0256 215/256 |
| 4,947,245 A * | 8/1990 | Ogawa | A61B 1/00101 348/66 |
| 5,004,879 A | 4/1991 | Bernhardt et al. | |
| 5,322,518 A * | 6/1994 | Schneider | A61M 39/24 604/167.03 |
| 5,430,266 A | 7/1995 | Austin, Jr. et al. | |
| 5,587,736 A * | 12/1996 | Walls | A61B 1/042 348/65 |
| 5,609,561 A * | 3/1997 | Uehara | A61B 1/042 348/75 |
| 5,611,769 A * | 3/1997 | Monroe | A61B 1/042 348/73 |
| 5,728,986 A | 3/1998 | Bennett et al. | |
| 5,777,281 A | 7/1998 | Riddiford | |
| 5,868,664 A * | 2/1999 | Speier | A61B 1/042 348/73 |
| 6,106,457 A * | 8/2000 | Perkins | A61B 1/00041 396/312 |
| 6,204,463 B1 | 3/2001 | Stringos | |
| 6,459,057 B1 | 10/2002 | Domzalski | |
| 6,461,352 B2 | 10/2002 | Morgan et al. | |
| 6,500,169 B1 | 12/2002 | Deng | |
| 6,573,466 B1 | 6/2003 | Rapp et al. | |
| 6,608,270 B2 | 8/2003 | Donofrio et al. | |
| 6,635,838 B1 | 10/2003 | Kornelson | |
| 6,752,816 B2 | 6/2004 | Culp et al. | |
| 7,097,058 B2 * | 8/2006 | Wellman | B65D 47/0828 215/217 |
| 7,282,657 B2 | 10/2007 | Wimmer et al. | |
| 7,306,592 B2 | 12/2007 | Morgan et al. | |
| 7,387,214 B1 * | 6/2008 | Shingle | B65D 41/06 215/206 |
| 7,600,427 B2 * | 10/2009 | Palmer | G01D 11/26 220/298 |
| 7,608,039 B1 | 10/2009 | Todd | |
| 7,705,258 B2 | 4/2010 | Geldmacher | |
| 7,731,050 B2 * | 6/2010 | Parks | B65D 21/0219 206/509 |
| 7,835,634 B2 | 11/2010 | Berend et al. | |
| 8,056,751 B2 * | 11/2011 | Vovan | B65D 21/0222 206/508 |
| 8,066,132 B2 * | 11/2011 | Swift | A61C 1/0084 215/331 |
| 8,115,126 B2 | 2/2012 | Deng et al. | |
| 8,579,140 B2 * | 11/2013 | Delagrange | B65D 41/06 215/221 |
| 8,746,485 B1 * | 6/2014 | Tiefenthaler | B60K 15/0406 220/254.1 |
| 2002/0121519 A1 * | 9/2002 | Martin | B01D 29/96 220/296 |
| 2004/0042779 A1 * | 3/2004 | Maeda | H04N 5/2252 396/79 |
| 2005/0145629 A1 * | 7/2005 | Herr | B65D 41/06 220/293 |
| 2006/0235377 A1 | 10/2006 | Earley et al. | |
| 2007/0017891 A1 * | 1/2007 | Herr | B65D 55/066 215/228 |

FOREIGN PATENT DOCUMENTS

| | | |
|---|---|---|
| FR | 2 800 195 A1 | 4/2001 |
| WO | WO 94/18686 A1 | 8/1994 |
| WO | WO 2006/111021 A1 | 10/2006 |

OTHER PUBLICATIONS

Stryker 1288 HD Video Camera User Guide (52 pages).
Stryker 1288 HD Urology Camera Head User Guide (26 pages).

* cited by examiner

TAMPER-EVIDENT CAMERA ENCLOSURE

CROSS REFERENCE TO RELATED APPLICATION

This application claims the benefit of U.S. Provisional Application Ser. No. 61/782,099, filed Mar. 14, 2013, which is incorporated herein by reference in its entirety.

BACKGROUND OF THE INVENTION

The present invention generally relates to a housing configuration for a medical instrument or tool, and more specifically to a sealed, tamper-evident housing for a camera head to be used with an endoscopic system.

Medical instruments or tools are utilized during surgery for various purposes. Some of these surgical tools may be used in what are generally termed endoscopic procedures. Endoscopy in the medical field allows internal features of the body of a patient to be viewed without the use of traditional, fully invasive surgery. Endoscopic imaging systems incorporate endoscopes so as to enable a surgeon to view a surgical site, and endoscopic tools enable non-invasive surgery at the site. Such tools may be shaver-type devices which mechanically cut bone and hard tissue, or radio frequency (RF) probes which are used to remove tissue via ablation or to coagulate tissue to minimize bleeding at the surgical site, for example.

In endoscopic surgery, the endoscope is placed in the body at the location at which it is necessary to perform a surgical procedure. Other surgical instruments, such as the endoscopic tools mentioned above, are also placed in the body at the surgical site. A surgeon views the surgical site through the endoscope in order to manipulate the tools to perform the desired surgical procedure. Some endoscopes are usable along with a camera head for the purpose of processing the images received by the endoscope. The eye piece of such an endoscope is typically coupled to a camera head, which is connected to a camera control unit.

The development of endoscopes and their companion surgical tools has made it possible to perform minimally invasive surgery that eliminates the need to make a large incision in the patient to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

Because the endoscope system, including the camera head, is involved in a surgical procedure, care must be taken to ensure that the components are not only sealed, but also that the areas of the components that may accumulate matter, such as tissue or blood, are minimized or eliminated. In the past, camera heads have comprised a two-piece housing, the pieces being screwed or bolted together. While the use of screws or bolts allows for adequate attachment and sealability of the camera housing, it provides small areas or pockets in which matter can accumulate. These areas or pockets thus can possibly result in a less than sanitary system, and areas which are not easily cleaned and sanitized.

The embodiments of the present invention solve the above-described problems. One embodiment of the present invention is directed to a two-piece housing including a first enclosure part and a second enclosure part. The first enclosure part has a plurality of locking areas and optionally, one or more mating grooves. The second enclosure part has a plurality of locking tabs and optionally, one or more mating tabs. The locking tabs engage the locking areas of the first enclosure to lock the parts together, and the mating tabs fit within the mating grooves of the first enclosure part to add stability and to make the housing tamper-evident.

Another embodiment of the present invention is directed to a method of assembling a camera head housing made of two parts, a first enclosure piece and a second enclosure piece. The two enclosure pieces are attached to one another by the use of a specialized tool to fit the first enclosure piece onto the second enclosure piece in a rotatable fashion, which creates a snug friction fit and a seal without the use of any fasteners other than internal flanges, grooves, and tabs on the housing components.

Other advantages, objects and/or purposes of the invention will be apparent to persons familiar with constructions of this general type upon reading the following specification and inspecting the accompanying drawings.

DETAILED DESCRIPTION

Figure 1:
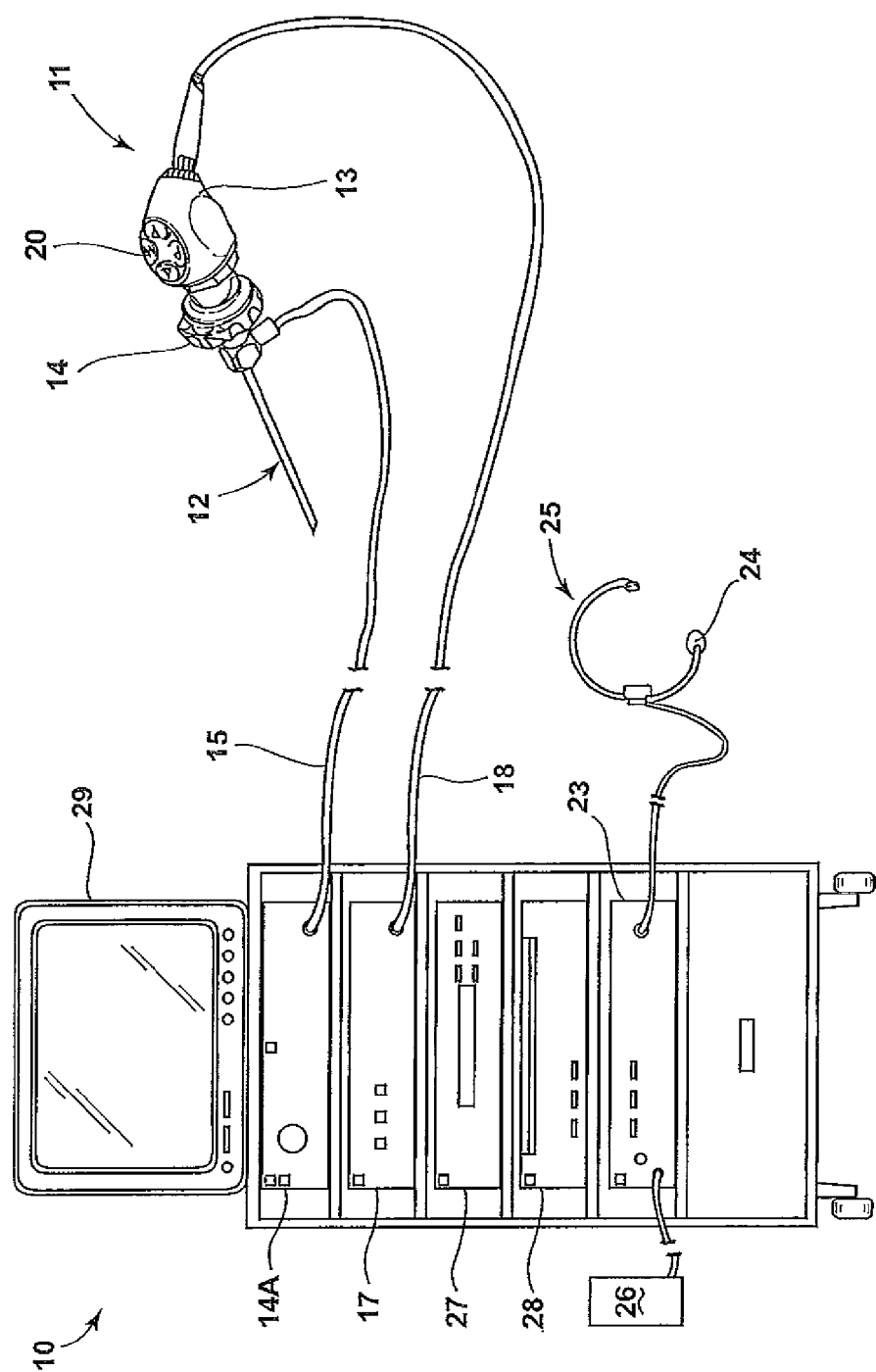
FIG. 1 is an illustration of an endoscopic camera arrangement including an example of one type of scope assembly incorporating a sealed camera head according to the invention.

Certain terminology will be used in this description for convenience and reference only, and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. This terminology will include the words specifically mentioned, derivatives thereof, and words of similar import.

FIG. 1 shows an endoscopic camera arrangement 10, including a scope assembly 11 which may be utilized in endoscopic procedures. The scope assembly 11 incorporates an endoscope or scope 12 which is coupled to a camera head 13 by a coupler 14 located at the distal end of the camera head 13. Light is provided to the scope by a light source 14A via a light conduit 15, such as a fiber optic cable. The camera head 13 is coupled to a camera control unit (CCU) 17 by a transmission cable 18. Operation of the camera 13 is controlled, in part, by the CCU 17. The cable 18 conveys video image data from the camera head 13 to the CCU 17 and conveys various control signals bi-directionally between the camera head 13 and the CCU 17. In one embodiment, the image data output by the camera head 13 is digital, in which the cable 18 may be a FireWire, a universal serial bus (USB), or other type of high-speed digital interface.

A control or switch arrangement 20 is provided on the camera head 13 and allows a user to manually control various functions of the arrangement 10. These and other functions may also be controlled by voice commands using a voice-control unit 23, which is coupled to the CCU 17. Voice commands are input into a microphone 24 mounted on a headset 25 worn by the surgeon and coupled to the voice-control unit 23. A hand-held control device 26, such as a tablet with a touch screen user interface or a PDA, may be coupled to the voice control unit 23 as a further control interface. In the illustrated embodiment, a recorder 27 and a printer 28 are also coupled to the CCU 17. Additional devices, such as an image capture and archiving device, may be included in arrangement 10 and coupled to the CCU 17. Video image data acquired by the camera head 13 and processed by the CCU 17 is converted to images, which can be displayed on a monitor 29, recorded by recorder 27, and/or used to generate static images, hard copies of which can be produced by printer 28.

Figure 2:
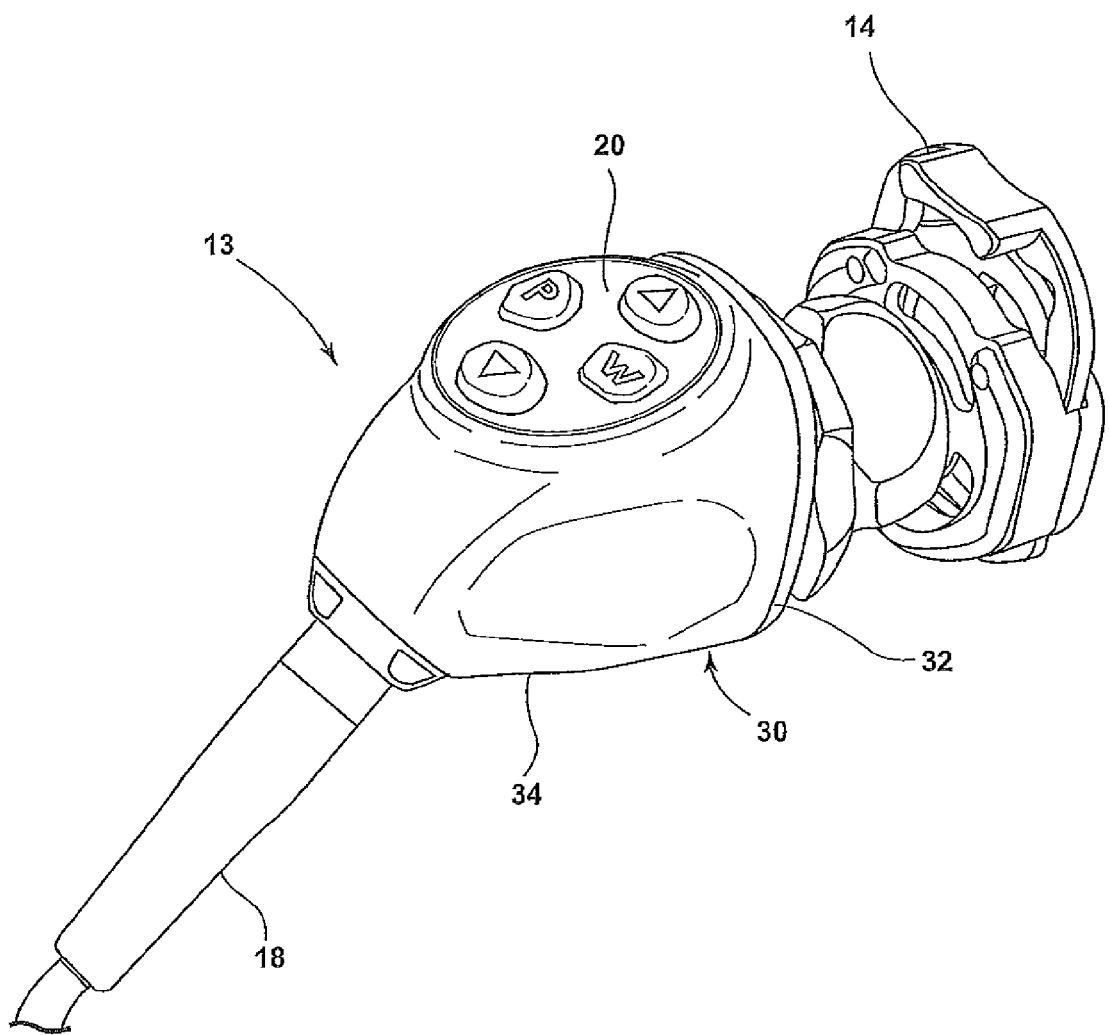
FIG. 2 is a perspective view of the camera head, coupler, and transmission cable of the endoscopic arrangement of FIG. 1.
Figure 3:
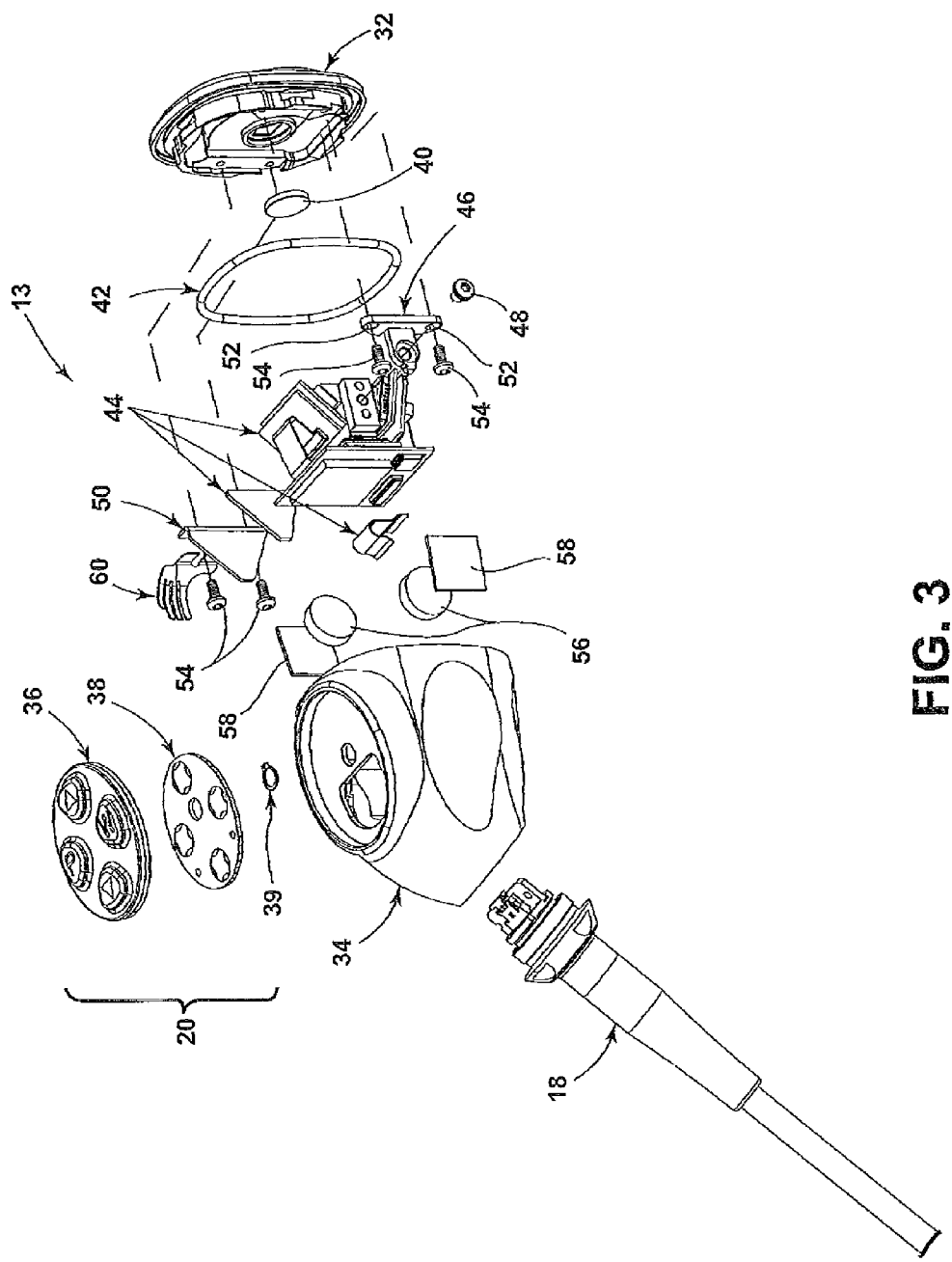
FIG. 3 is a perspective exploded view of the camera head of FIG. 2.

As shown in FIGS. 2-3, the camera head 13 includes a housing 30. The housing 30 generally has two parts, a front enclosure part 32 and a rear enclosure part 34. The control or switch arrangement 20 is sealably attached to the rear enclosure part 34, as described, for example, in commonly-owned U.S. Pat. No. 8,115,126, which is hereby incorporated by reference in its entirety. As shown in FIG. 3, the control or switch arrangement 20 includes a 4-button keypad 36, a 4-button membrane switchboard 38, which work in tandem to manually control the functions of the camera, and a snap ring 39.

The internal components of the camera head 13 include a window 40, which is preferably sealably attached to the front enclosure part 32. An O-ring 42 engages the front enclosure part 32 and is used to seal the housing upon assembly, which is described below. A 3-chip camera unit 44 is attached to a prism bracket 46 by the use of a fastener 48, such as a pan-head torx machine screw. A second bracket 50 is also attached to the camera unit 44. The brackets 46, 50 have apertures 52 which allow fasteners 54, such as pan-head torx machine screws, to attach the brackets 46, 50, and thus the camera unit 44, to the front enclosure part 32. The camera head 13 also includes a pair of desiccant tablets 56 which may be attached to the housing 30 by any common means such as use of foam tape 58. A connection spring 60 is also preferably attached to the camera unit 44 via the bracket 50 to allow engagement of the camera unit 44 with the rear enclosure part 34.

The camera unit 44, through the rear enclosure part 34, is attached to the transmission cable 18 for connection with the CCU 17, as described above.

Figure 5:
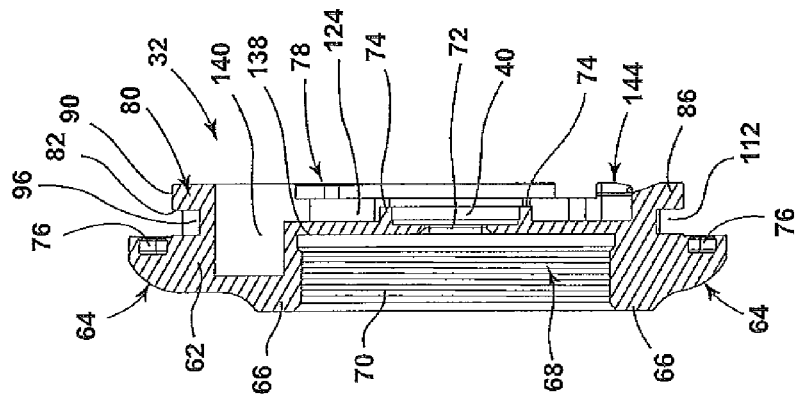
FIG. 5 is a side elevational cross-sectional view of the front enclosure part of the housing of the camera head of FIG. 2, taken along lines V-V in FIG. 4.
Figure 4:
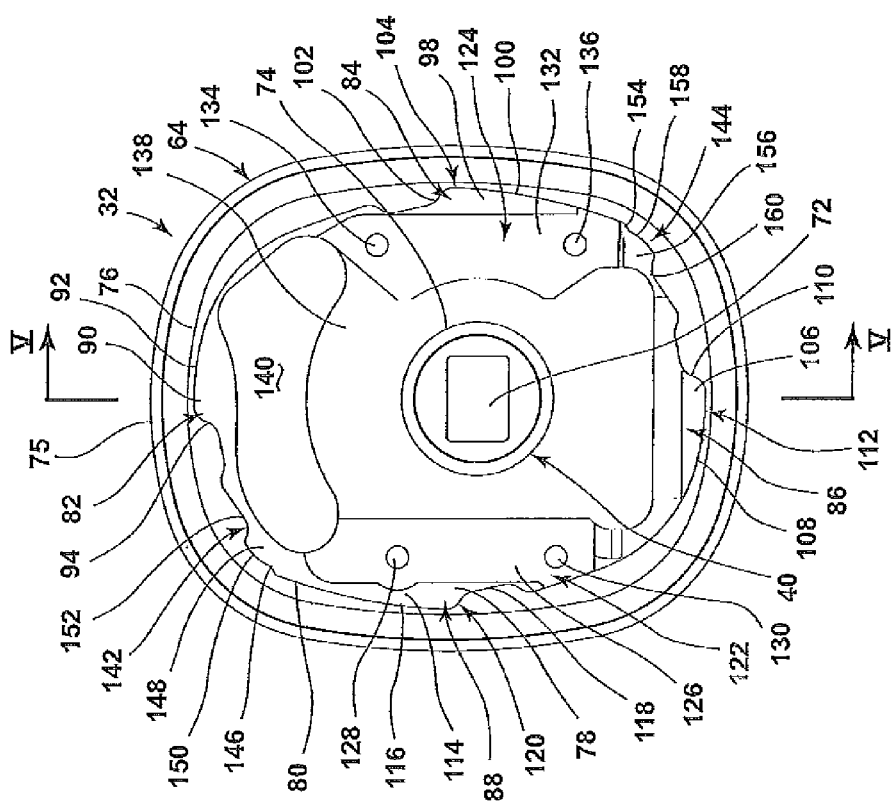
FIG. 4 is a front elevational view of a front enclosure part of the housing of the camera head of FIG. 2.

FIGS. 4-5 depict the front enclosure part 32 in further detail. The front enclosure part 32 is preferably a monolithic structure made of a rigid lightweight material such as aluminum. The front enclosure part 32 includes an outer shell portion 62, the periphery 64 of which is visible and contactable by the user when the camera head 13 is in the assembled state. A circular rim 66 defines a large bore 68 extending from the periphery 64 inwardly toward the center of the camera head 13, thus creating a substantially cylindrical space in the outer shell portion 62 of the front enclosure part 32. The large bore 68 preferably includes threads 70 in its inner diameter to allow connection to the coupler 14, the endoscope 12, or other instrument. The large bore 68 terminates axially at an inner wall 138. The inner wall 138 has a viewing hole 72, in the radial center of the large bore 68, which is preferably rectangular in shape. The viewing hole 72 allows transportation of images from the endoscope 12 into the camera head housing 30 to the camera unit 44.

Figure 6:
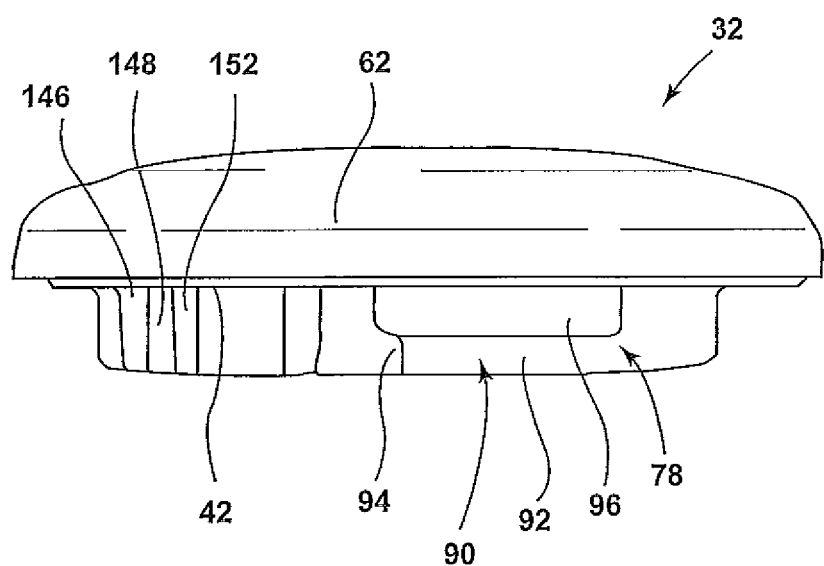
FIG. 6 is a top plan view of the front enclosure part of the housing of the camera head of FIG. 2.

On the interior of the front enclosure part 32, extending adjacent the perimeter of the front enclosure part 32 is a face 75, and radially interiorly of the face 75 is a channel 76 for receiving and holding the O-ring 42. The channel 76 is unitary and sized and shaped such that the O-ring 42 extends slightly beyond the channel 76 in the axial, inward direction. Radially inwardly of the channel 76 is a connection member 78 which extends generally axially inwardly from the outer shell 62. As shown in FIGS. 4-6, the connection member 78 has a peripheral portion 80 which generally follows the peripheral shape of the outer shell portion 62, but is irregularly shaped. The connection member 78 includes four holding or mating members. A first holding member 82 is adjacent the top of the front enclosure part 32, as the front enclosure part 32 is oriented in FIG. 4. A second holding member 84 is adjacent the right side periphery of the front enclosure part 32, as the front enclosure part 32 is oriented in FIG. 4. A third holding member 86 is adjacent the bottom of the front enclosure part 32, as the front enclosure part 32 is oriented in FIG. 4. A fourth holding member 88 is adjacent the left periphery of the front enclosure part 32, as the front enclosure part 32 is oriented in FIG. 4.

The first holding member 82 includes an axially inwardly disposed flange 90 which has an outer gently-curved portion 92 at its periphery and an inwardly angled portion 94, angled toward the center of the front enclosure part 32, moving away from the gently-curved portion 92. Located axially outwardly from the flange 90 is a holding channel 96 between the flange 90 and the outer shell portion 62 of the front enclosure part 32 (see FIGS. 5-6). The holding channel 96 is sized and shaped to receive a mating tab, which is described below. The second holding member 84 includes a flange 98 which has a gently-curved portion 100 at its periphery and an inwardly angled portion 102, angled toward the center of the front enclosure part 32, moving away from the gently-curved portion 100. Between the flange 98 and the outer shell portion 62 of the front enclosure part 32 is a holding channel 104 that is sized and shaped to receive a mating tab, which is described below. The third holding member 86 includes a flange 106 which has a gently-curved portion 108 at its periphery and an inwardly angled portion 110 angled toward the center of the front enclosure part 32, moving away from the gently-curved portion 108. Between the flange 106 and the outer shell portion 62 of the front enclosure part 32 is a holding channel 112 that is sized and shaped to receive a mating tab, which is described below. The fourth holding member 88 includes a flange 114 that has a gently-curved portion 116 at its periphery and an inwardly angled portion 118, angled toward the center of the front enclosure part 32, moving away from the gently-curved portion 116. Between the flange 114 and the outer shell portion 62 of the front enclosure part 32 is a holding channel 120 which is sized and shaped to receive a mating tab, which is described below.

Radially inwardly of the connection member 78 are a first side portion 122 and a second side portion 124. The first side portion 122 and the second side portion 124 generally oppose each other on sides (left and right) of the front enclosure part 32. The first side portion 122 has a surface 126 which is located axially outwardly from the axially inner surface of connection member 78. The first side portion 122 has two apertures 128, 130 therein, which are each preferably threaded and adapted to receive the fasteners 54 such as pan-head torx machine screws, for attachment of the second bracket 50 to the front enclosure part 32. The second side portion 124 has a surface 132 that is preferably in the same plane as the surface 126. Like the first side portion 122, the second side portion 124 has two apertures 134, 136, which are preferably threaded and adapted to receive the fasteners 54 such as pan-head torx machine screws, for attachment of the prism bracket 46 to the front enclosure part 32.

The inner wall 138 has a flat surface in a plane parallel to, and axially outwardly-located with respect to, the plane of the surfaces 126, 132. A circular rim 74 extends axially inwardly from the surface of the inner wall 138. The circular rim 74 is positioned around the viewing hole 72 such that the window 40 may be positioned and held within the space defined by the circular rim 74 adjacent the viewing hole 72. Together with the connection member 78, the inner wall 138 defines an opening 140, which provides a space for receiving a portion of the camera unit 44.

The connection member 78 also defines two locking portions, a first locking portion 142 and a second locking portion 144, which are preferably located on opposing corners from each other. As shown in FIGS. 4 and 6, the first locking portion 142 includes a small groove 146 sized to receive a locking tab of the rear enclosure part 34. The small groove 146 is defined on one side by the peripheral portion 80 of the connection member 78 and on the other side by a ridge 148. The ridge 148 includes a small elevated portion 150, which extends radially outwardly with respect to the small groove 146 in the form of a small bump. On the opposite side of the ridge 148, with respect to the small groove 146, is a large groove 152. The large groove 152 is sized and shaped to receive and hold a locking tab of the rear enclosure part 34. The second locking portion 144 preferably has an identical structure to that of the first locking portion 142. The second locking portion 144 has a small groove 154 in which a locking tab of the rear enclosure part 34 may be received. The small groove 154 is defined on one side by the peripheral portion 80 of the connection member 78 and on the other by a ridge 156. The ridge 156 has an elevated portion 158, extending radially outwardly with respect to the small groove 154, in the form of a small bump. On the opposite side of the ridge 156, with respect to the small groove 154, is a large groove 160. The large groove 160 is sized and shaped to receive and hold a locking tab of the rear enclosure part 34.

Figure 8:
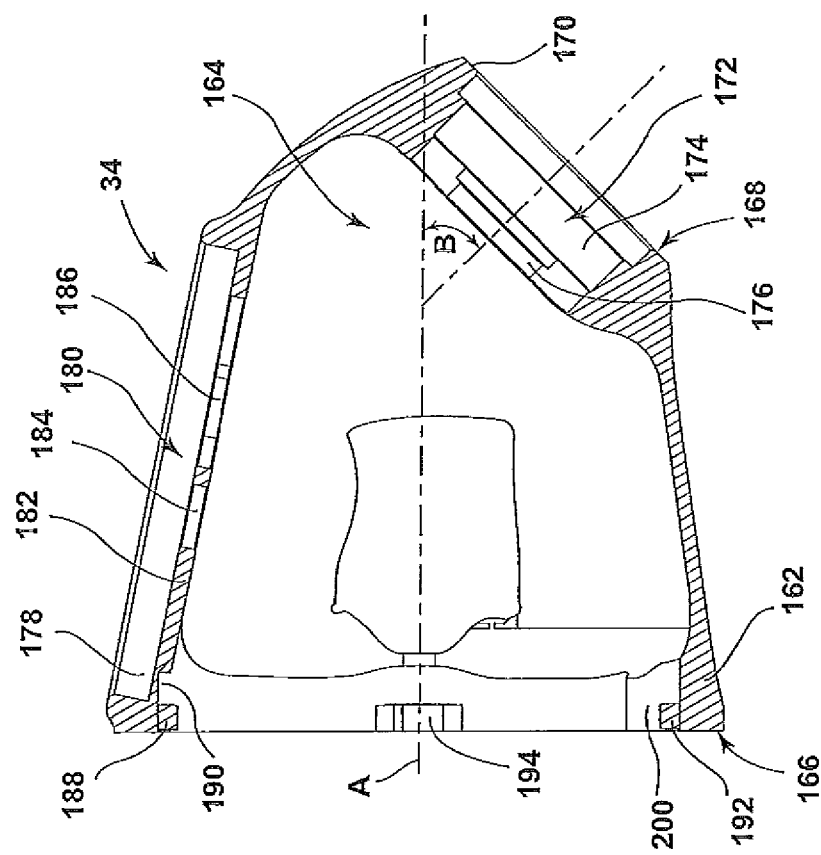
FIG. 8 is a side elevational cross-sectional view of the rear enclosure part of the housing of the camera head of FIG. 2, taken along lines VIII-VIII in FIG. 7.
Figure 7:
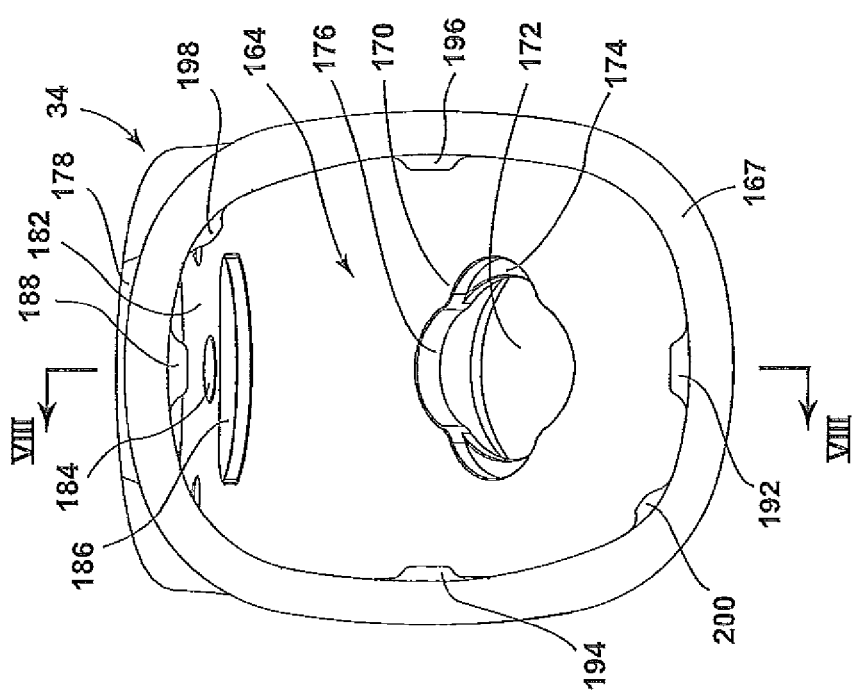
FIG. 7 is a front elevational view of a rear enclosure part of the housing of the camera head of FIG. 2.

FIGS. 7-8 depict the rear enclosure part 34 in detail. The rear enclosure part 34 is preferably a monolithic structure made of a rigid lightweight material such as aluminum. The rear enclosure part 34 is sized and shaped to allow the majority of the camera components, including the camera unit 44, to be received and held therein. The rear enclosure part 34 has an outer wall 162 which defines a space 164 therein. The rear enclosure part 34 terminates in a first end 166 defining an axially oriented face 167, which is preferably substantially in a single plane. The rear enclosure part 34 has a longitudinal axis A which is generally perpendicular to the face 167. The area of the outer wall 162 adjacent the first end 166 is preferably slightly thicker than the remainder of the outer wall 162 in order to provide a secure attachment and proper seal when attached to the front enclosure part 32. The rear enclosure part 34 is generally frustoconical in shape and terminates in a second end 168 which is opposite the first end 166.

The second end 168 includes a circular rim 170 which defines an opening 172 as shown in FIG. 8. The opening 172 extends along an axis that is at an angle B with respect to the longitudinal axis A (see FIG. 8). In one embodiment, the angle B is about 45°, as shown in FIG. 8. In another embodiment (not shown), angle B is about 0°, or in other words, the longitudinal axis of the opening 172 is parallel to the longitudinal axis A. The opening 172 is further defined by an inner rim 174 which is disposed inwardly from the circular rim 170. The inner rim 174 is preferably circular and defines a circular space that has a smaller diameter than the diameter of the circular space defined by the circular rim 170. Adjacent the inner rim 174 is a generally clover leaf shaped rim 176 which defines an even smaller space. The opening 172 is sized and shaped to receive an end of the transmission cable 18 for temporary or permanent attachment of the camera unit 44 thereto.

At the top of the rear enclosure part 34 is an upper lip 178, which is generally oval in shape and defines a button control space 180. The button control space 180 terminates at a button control floor 182. The button control floor 182 has two apertures therein. A first aperture 184 is a small circular aperture positioned more toward the first end 166 of the rear enclosure part 34. The second aperture 186 is a large aperture positioned more toward the second end 168 of the rear enclosure part 34. Both of the apertures 184, 186 are sized and shaped to allow electrical components to extend therethrough for attachment to the membrane switchboard 38. The button control space 180 is sized and shaped to receive both the 4-button membrane switchboard 38 and at least a portion of the 4-button keypad 36 in a sealed arrangement.

Adjacent the first end 166 of the rear enclosure part 34 are a plurality, preferably four, mating tabs for use in attaching the front enclosure part 32 to the rear enclosure part 34. A first mating tab 188 extends downwardly from an area adjacent the top of the rear enclosure part 34. Behind the first mating tab 188 is a channel 190 configured to receive flange 90 of the front enclosure part 32 therein. The first mating tab 188 is generally trapezoidal in shape and is sized and shaped to fit within the holding channel 96 of the front enclosure part 32. A second mating tab 192 extends upwardly from an area adjacent the bottom of the rear enclosure part 34. The second mating tab 192 is generally trapezoidal in shape and is configured to fit within the holding channel 112 of the third locking member 86 of the front enclosure part 32. A third mating tab 194 extends radially inwardly from an area adjacent the left side of the rear enclosure part 34, as the rear enclosure part 34 is oriented in FIG. 7. The third mating tab 194 is generally trapezoidal in shape and is configured to fit within the holding channel 104 of the second locking member 84 of the front enclosure part 32. A fourth mating tab 196 extends radially inwardly from an area adjacent the right side of the rear enclosure part 34, as the rear enclosure part 34 is oriented in FIG. 7. The fourth mating tab 196 is generally trapezoidal in shape and is configured to fit within the holding channel 120 of the fourth locking member 88 of the front enclosure part 32.

The rear enclosure part 34 also includes two diagonally-oriented opposing locking tabs. The first locking tab 198 is located adjacent the upper right corner of the rear enclosure part 34, as the rear enclosure part 34 is oriented in FIG. 7. In the opposite corner, i.e. the bottom left corner of the rear enclosure part 34 as the rear enclosure is oriented in FIG. 7, is a second locking tab 200. The first and second locking tabs 198, 200 are also generally trapezoidal in shape although slightly smaller in cross-section than the first, second, third, and fourth mating tabs 188, 192, 194, 196, and also extend further axially toward the second end 168 of the rear enclosure part 34 than the first, second, third, and fourth mating tabs.

It is contemplated that a different number of holding tabs and locking tabs may be employed, depending on the structure of the housing components. Moreover, it is contemplated that the locking areas, channels and tabs may have different shapes than those described herein.

To assemble the camera head, preferably one or more tools are used to achieve the requisite torque to adequately attach the front enclosure part 32 to the rear enclosure part 34, while achieving a sealed and tamper-evident assembly.

Figure 9:
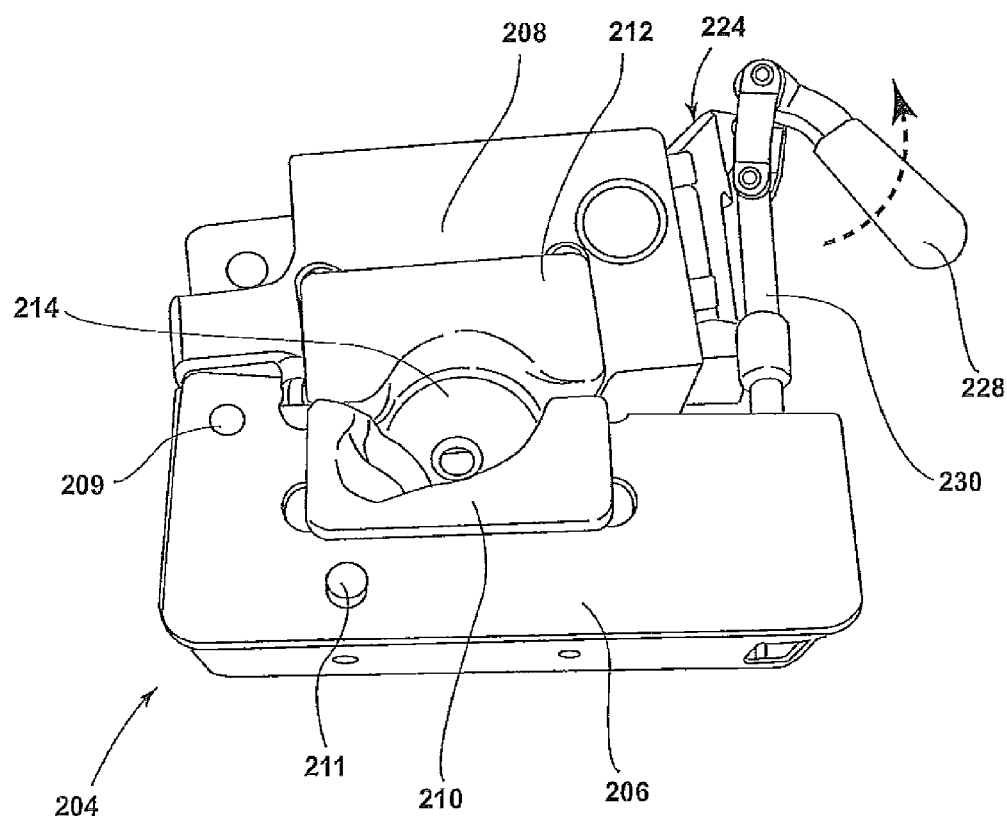
FIG. 9 is a perspective view of a rear enclosure compression tool in an unclamped position.
Figure 10:
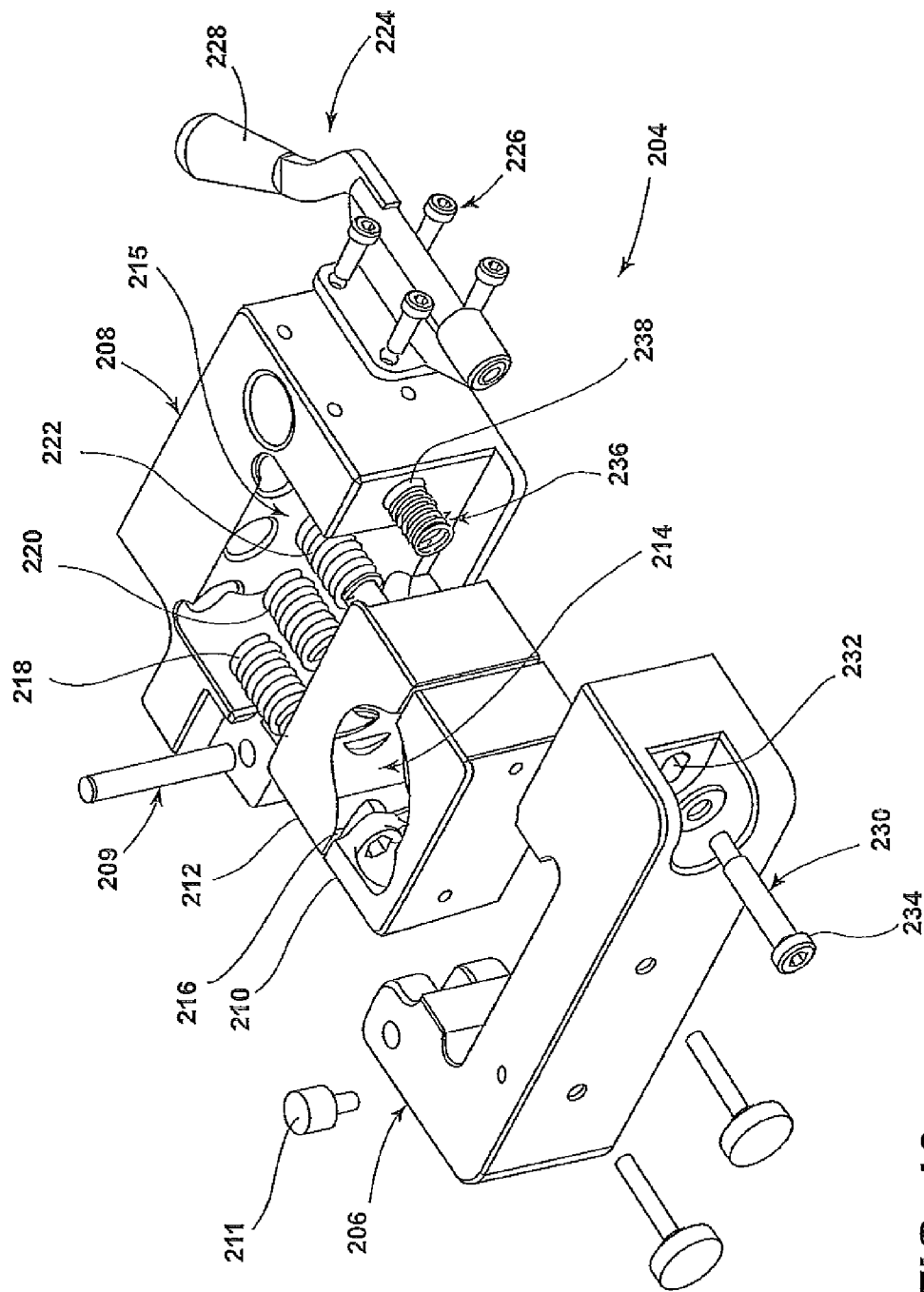
FIG. 10 is a perspective exploded view of the rear enclosure compression tool of FIG. 9.

A first such tool is a rear enclosure compressor 204, which is depicted in FIGS. 9-10. The rear enclosure compressor 204 includes a first swivel base 206 and a second base 208. The first swivel base 206 is swivelable with respect to the second base 208 about a swivel pin 209. The first swivel base 206 has an inner compartment in which a first seat portion 210 resides. The first seat portion 210 has a thumb screw 211 attached to it to ensure that the front enclosure part 32 is attached to the rear enclosure part 34 in the proper alignment. The second base 208 has an opposing inner compartment in which a second seat portion 212 resides. Together, the first seat portion 210 and the second seat portion 212 define an interior seat 214 in which the rear enclosure part 34 fits. A biasing assembly 215 is attached to the second base 208 and the second seat portion 212 by a shoulder screw 216, and includes three springs 218, 220, 222. The springs 218, 220, 222 bias the first seat portion and the second seat portion toward each other. A toggle clamp 224 is attached to the base 208 by bolts 226. The toggle clamp 224 has a swivelable toggle handle 228, which is connected to a rod section 230. The rod section 230 extends through an aperture 232 in the first swivel base 206. The rod section 230 terminates in a head 234 which has a diameter that is larger than that of the aperture 232. A compression spring 236 is positioned between the first swivel base 206 and the second base 208, and which may at least partially reside in a bore 238 in the second base 208.

For actuation of the compression, the handle 228 can be moved in the direction of the arrow shown in FIG. 9. Movement of the handle 228 in the direction of the arrow (counter-clockwise) pulls the rod 230, and in turn the first swivel base 206, toward the second base 208 about swivel pin 209, resulting in a second, compression position.

Figure 11:
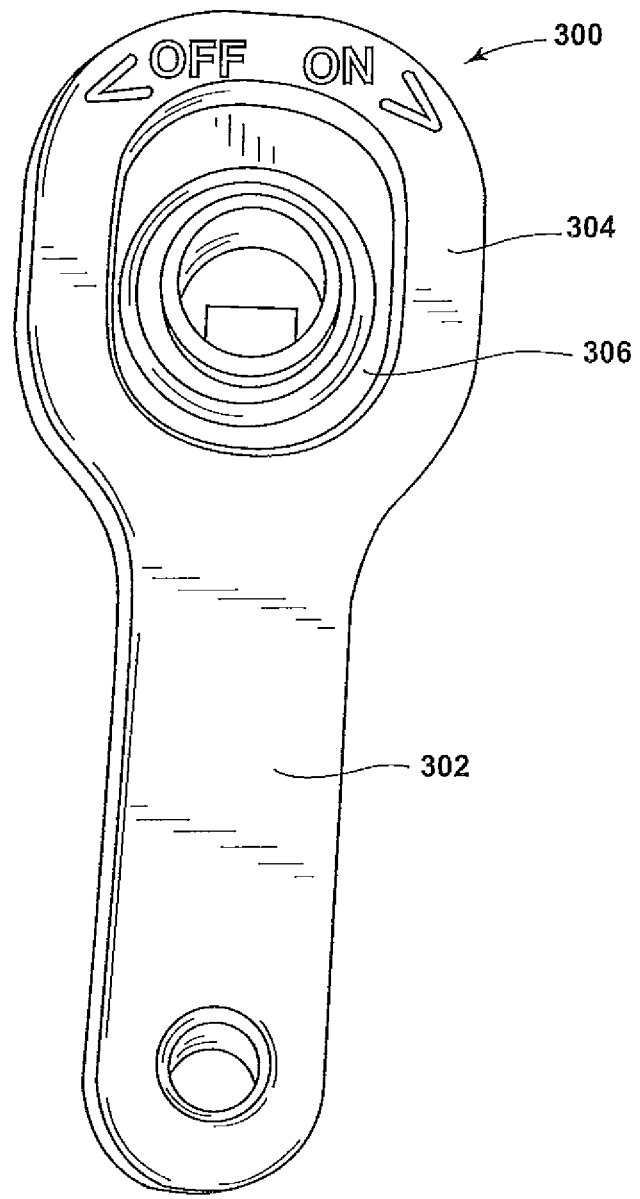
FIG. 11 is an elevational view of a front enclosure wrench tool.

A second tool which may be used to assist in assembly of the camera head housing 30 is a wrench 300 shown in FIG. 11. The wrench 300 includes a handle 302 and a head portion 304. The head portion 304 includes a space 306 therein especially sized and shaped to receive a portion of the front enclosure part 32, and to hold the front enclosure part 32 therein.

Figure 12:
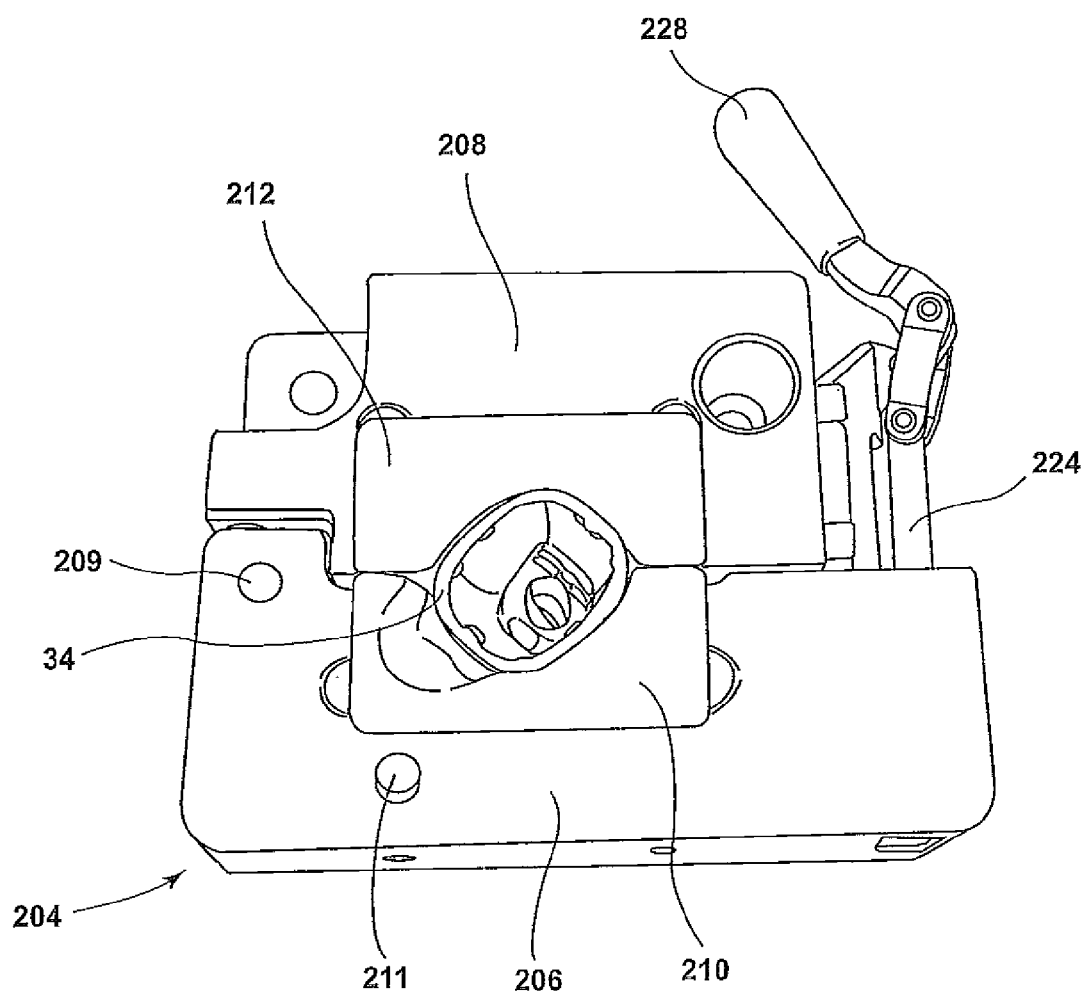
FIG. 12 is a perspective view of the rear enclosure compression tool of FIGS. 9-10, in a clamped position with a rear enclosure part of the housing of the camera head of FIG. 2 therein.

For assembly of the camera head housing 30, the rear enclosure compressor 204 is provided in the open position. The rear enclosure part 34 is placed into the seat 214 of the rear enclosure compressor 204. The handle 228 of the toggle clamp 224 is then rotated to move the first base 206 and second base 208 toward one another, adjusting the rear enclosure compressor 204 to the second, compression position and locking the rear enclosure part 34 in the seat 214, as shown in FIG. 12. In this position, the rear enclosure compressor 204 compresses the rear enclosure part 34 in a diagonal direction, distorting the shape of the rear enclosure part 34 slightly. The distortion of the rear enclosure part 34 is on the order of a few thousandths of an inch. The compression, and thus distortion of the rear enclosure part 34, is determined by the biasing force of the three springs 218, 220, 222. The springs 218, 220, 222 are enclosed within the structure of the rear enclosure compressor 204, and thus the compression force is thus not adjustable by a user.

Figure 13:
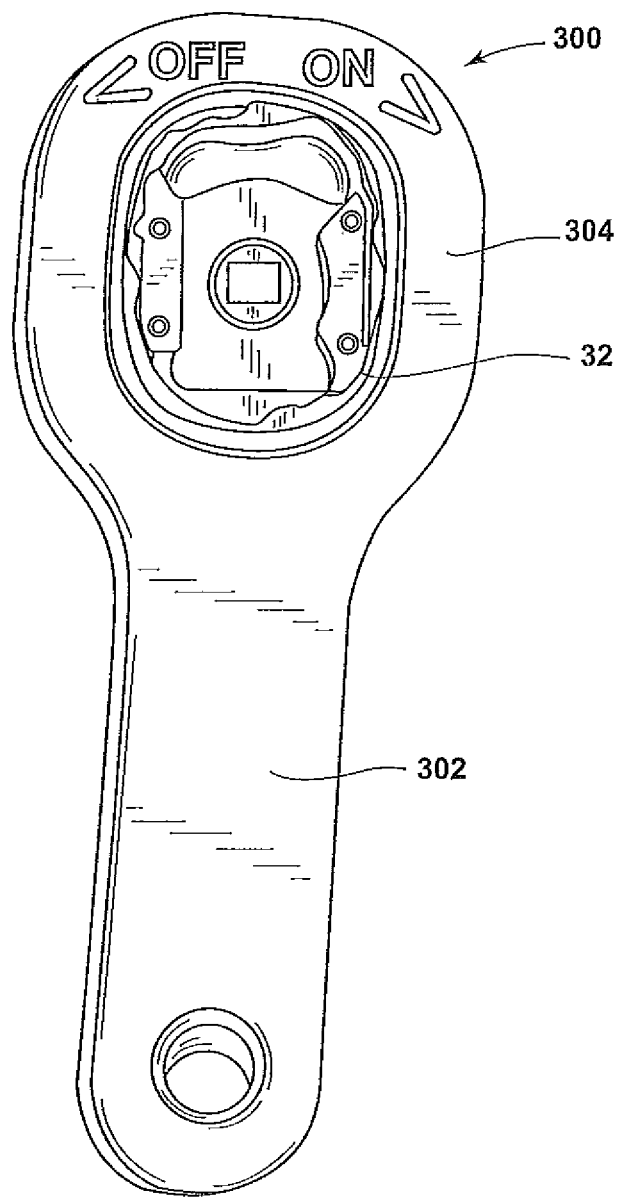
FIG. 13 is an elevational view of the front enclosure wrench tool of FIG. 11, engaged with a front enclosure part of the housing of the camera head of FIG. 2.

Once the rear enclosure part 34 is locked in place in the seat 214 (and the other components of the camera are inserted or attached), the front enclosure part 32 is placed within the space 306 of the wrench 300, as shown in FIG. 13. The wrench 300 can then be turned over and the front enclosure part 32 placed against the rear enclosure part 34. The front enclosure part 32 and the rear enclosure part 34 are then aligned such that the locking tab 198 fits into the small groove 146 of the first locking portion 142 of the front enclosure part 32, and the locking tab 200 fits within the small groove 154 of the second locking portion 144 of the front enclosure part 32. In addition, the first mating tab 188 fits into a space adjacent the first holding member 82, the second mating tab 192 fits into a space adjacent the third holding member 86, the third mating tab 194 fits into a space adjacent the second holding member 84, and the fourth mating tab 196 fits into a space adjacent the fourth holding member 88.

Figure 14:
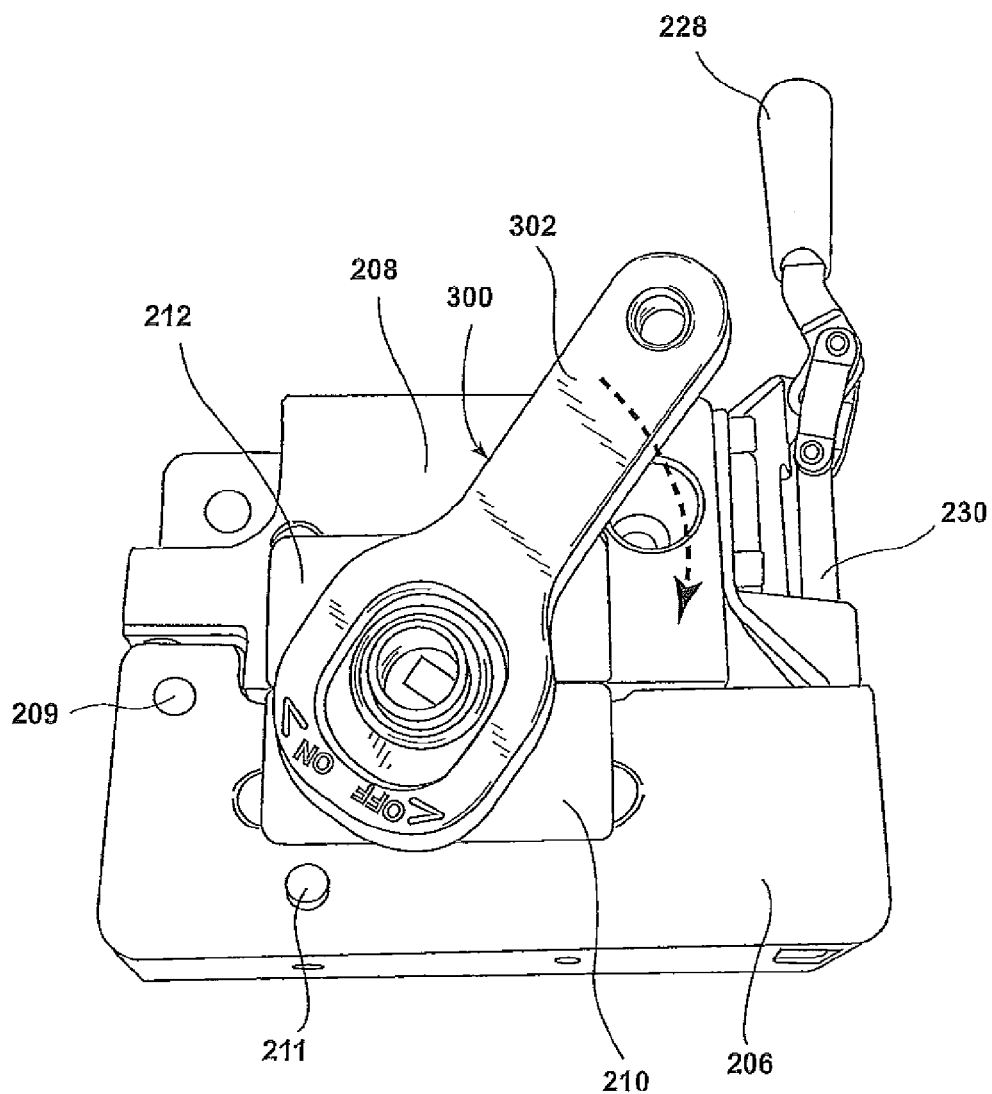
FIG. 14 is a perspective view of the rear enclosure compression tool of FIGS. 9-10, in use with the front enclosure wrench tool of FIG. 11.

Once the front enclosure part 32 and the rear enclosure part 34 are aligned in this manner, the faces 75, 167 of the front enclosure part 32 and the rear enclosure part 34, respectively, should be touching. To complete the assembly, the wrench 300 is then rotated in the direction of the arrow (clockwise) in FIG. 14, relative to the rear enclosure compressor 204. Upon rotation of the wrench 300, the first mating tab 188 rotates into the holding channel 96 behind the flange 90, the second mating tab 192 rotates into the holding channel 112 behind the flange 106, the third mating tab 194 rotates into the holding channel 104 behind the flange 98, and the fourth mating tab 196 rotates into the holding channel 120 behind the flange 114. In addition, to create a locking effect, the first locking tab 198 rotates out of the small groove 146, past the ridge 148 without engagement, and into the large groove 152 where the first locking tab 198 is held in place by the structure of the ridge 148 after the unit is released from the rear enclosure compressor 204. Likewise, the second locking tab 200 rotates out of the small groove 154, past the ridge 156 without engagement, and into the large groove 160, where the second locking tab 200 is held in place by the structure of the ridge 156 after the unit is released from the rear enclosure compressor 204.

Once the front enclosure part 32 is rotated into place with respect to the rear enclosure part 34, the wrench 300 is lifted away from the front enclosure part 32 and the handle 228 of the toggle clamp 224 is rotated in a clockwise direction to unlock the camera head 13 from the seat 214 and decompress the rear enclosure part 34. The assembled housing 30 of the camera head 13 can then be removed from the rear enclosure compressor 204 where additional assembly, such as assemblage of the switchboard 38 and keypad 36 may take place.

For disassembly of the housing 30 for maintenance, inspection, or otherwise, the assembled housing 30 is placed within the seat 214 of the rear enclosure holder 204 and the handle 228 of the toggle clamp 224 is rotated in a counter-clockwise direction to lock the housing 30 in place and to distort the rear enclosure part 34 slightly. The wrench 300 is then placed over the front enclosure part 32, fitting a portion of the front enclosure part 32 within the space 306 of the wrench head portion 304. The wrench 300 is then rotated in a counter-clockwise direction to remove the mating tabs from their respective holding channels and the locking tabs out of the large grooves, past the ridges, and into the small grooves of the locking portions 142, 144, leaving the front enclosure part 32 in an easily openable position with respect to the rear enclosure part 34. The front enclosure part 32 can then be lifted off of the rear enclosure part 34.

In the case where specialized tools such as the rear enclosure holder 204 and the wrench 216 are not used to disassemble the housing 30, a great deal of force will be required to remove the front enclosure part 32 from the rear enclosure part 34. If separated in the axial direction, such force will likely result in breakage of one or more of the components of either the front enclosure part 32 or the rear enclosure part 34, such as one or more mating tabs, one or more locking tabs, or one or more flanges. If such force is applied in a rotatable fashion without using the specialized wrench 300, in all likelihood the force necessary to open the housing 30 will result in damage to the exterior of either the front enclosure part 32 or the rear enclosure part 34, or both, in the process. This breakage or damage to the exterior of the housing 30, will result in evidence of tampering of the camera head housing 30. Even if care is taken to rotate the front enclosure part 32 with respect to the rear enclosure part 34, the rotation without compression will result in engagement of the locking tabs 198, 200 with the ridges 148, 156, scratching the ridges in the process. The scratches on ridges 148, 156 are evidence of tampering.

The described endoscopic camera assembly, including the novel camera head housing, is advantageous in that it uses no external components for assembly and sealing of the enclosure parts of the camera head housing. In addition, the structure results in a stable, secure, and tamper-evident product, ideal for use in endoscopic procedures.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. An endoscopic camera head having a longitudinal axis comprising:
    a first enclosure part having an outer shell and a member projecting axially from the outer shell, the member having a first locking area and a second locking area, the first locking area having a first ridge with at least one incline in the radial direction and a first groove adjacent the first ridge, and the second locking area having a second ridge with at least one incline in the radial direction and a second groove adjacent the second ridge;
    a second enclosure part having an outer wall, a first end, a second end, a first locking tab, and a second locking tab spaced from the first locking tab, the first end defining a first opening and the first locking tab and the second locking tab adjacent the first opening, the first locking tab residing at least partially within the first groove of the first locking area of the first enclosure part and being rotatably held in the first groove by the first ridge, the second locking tab residing at least partially within the second groove of the second locking area of the first enclosure part and being rotatably held in the second groove by the second ridge, the first enclosure part and the second enclosure part together forming a housing; and
    a camera unit disposed within the housing,
    the first enclosure part and the second enclosure part being shaped and sized such that the second enclosure part may be rotated with respect to the first enclosure part to cause engagement of the first locking tab with the first groove of the first locking area.

2. The endoscopic camera head of claim 1, the second enclosure part further comprising a first mating tab and a second mating tab for engagement with the first enclosure part.

3. The endoscopic camera head of claim 2, the first enclosure part further comprising a first mating channel and a second mating channel, the first mating channel receiving the first mating tab therein and the second mating channel receiving the second mating tab therein.

4. The endoscopic camera head of claim 3, the second enclosure part further comprising a third mating tab and a fourth mating tab for engagement with the first enclosure part.

5. The endoscopic camera head of claim 4, the first enclosure part further comprising a third mating channel and a fourth mating channel, the third mating channel receiving the third mating tab and the fourth mating channel receiving the fourth mating tab.

6. The endoscopic camera head of claim 1, the first enclosure part further comprising a generally peripheral O-ring channel, the O-ring channel holding a portion of an O-ring therein.

7. The endoscopic camera head of claim 1, wherein the second end of the second enclosure part defines a second opening.

8. A method of assembling an instrument housing having a longitudinal axis, the method comprising:
    providing a first enclosure part having an outer shell and member extending axially from the outer shell, the member having a first locking area and a second locking area, the first locking area having a first ridge and a first groove adjacent the first ridge, and the second locking area having a second ridge and a second groove adjacent the second ridge;
    providing a second enclosure part having an outer wall, a first end, a second end, a first locking tab, and a second locking tab spaced from the first locking tab, the first locking tab and the second locking tab adjacent the first end;
    providing a holding tool having a first member and a second member that are moveable toward each other to clamp the second enclosure part therein;

providing a rotating tool having a space therein sized and shaped to receive a portion of the first enclosure part, and a handle to assist in rotation of the rotating tool and the first enclosure part;

positioning a portion of the second enclosure part within the holding tool;

moving the first member of the holding tool toward the second member of the holding tool to clamp the second enclosure part;

engaging the first enclosure part with the second enclosure part by positioning the first locking tab adjacent the first ridge and positioning the second locking tab adjacent the second ridge; and rotating the rotating tool to move the first locking tab across the first ridge into the first groove, and to move the second locking tab across the second ridge into the second groove.

9. The method of claim 8, the second enclosure part further comprising a first mating tab and a second mating tab for engagement with the first enclosure part.

10. The method of claim 9, the first enclosure part further comprising a first mating groove and a second mating groove, the first mating groove receiving the first mating tab therein and the second mating groove receiving the second mating tab therein.

11. A kit for an instrument housing, the kit comprising:

a front enclosure piece having an outer member and an inner member projecting from the outer member, the inner member having an outer circumferential periphery, a first locking area, and a second locking area, the first locking area having a first ridge and a first groove adjacent the first ridge, the first ridge and the first groove having a surface defining a portion of the outer circumferential periphery of the inner member, and the second locking area having a second ridge and a second groove adjacent the second ridge, the second ridge and the second groove having a surface defining a portion of the outer circumferential periphery of the inner member; and a rear enclosure piece having an outer wall, a first end, a second end, a first locking tab, and a second locking tab, the first locking tab and the second locking tab each adjacent the first end and spaced apart from one another, the rear enclosure piece being capable of engagement with the front enclosure piece, and during engagement the rear enclosure piece being capable of rotation relative to the front enclosure piece, the rotation causing the first locking tab to move over the first ridge and into the first groove.

* * * * *